United States Patent [19]

Hainaut et al.

[11] 4,045,209

[45] Aug. 30, 1977

[54] SUBSTITUTED UREAS AS HERBICIDES

[75] Inventors: Daniel Hainaut, Villemomble; Jean-Pierre Demoute, Montreuil-Sous-Bois; Andre Teche, Paris, all of France

[73] Assignee: Roussel Uclaf, Paris, France

[21] Appl. No.: 615,401

[22] Filed: Sept. 22, 1975

Related U.S. Application Data

[63] Continuation-in-part of Ser. No. 582,877, June 2, 1975, abandoned, which is a continuation of Ser. No. 305,336, Nov. 10, 1972, abandoned.

[30] Foreign Application Priority Data

Nov. 17, 1971 France ............................. 71.41102

[51] Int. Cl.$^2$ .......................... A01N 9/12; C07C 119/00
[52] U.S. Cl. ......................................... 71/98; 71/88; 71/94; 71/95; 71/103; 71/120; 260/293.85; 260/326.82; 260/453 RW; 260/553 A; 544/159
[58] Field of Search ...................... 71/98; 260/453 RW

[56] References Cited

U.S. PATENT DOCUMENTS

| 3,112,342 | 11/1963 | Luckenbaugh | 260/453 R |
|---|---|---|---|
| 3,124,447 | 3/1964 | Wineman et al. | 71/98 |
| 3,165,549 | 1/1965 | Martin et al. | 260/453 R |
| 3,276,855 | 10/1966 | Richter | 71/98 |
| 3,288,586 | 11/1966 | Littler | 260/453 R |
| 3,502,705 | 3/1970 | Brown | 260/453 R |
| 3,652,630 | 3/1972 | Brown | 260/453 R |
| 3,654,357 | 4/1972 | Bretschneider et al. | 260/453 R |
| 3,697,572 | 10/1972 | Brown | 71/98 |
| 3,812,209 | 5/1974 | Brown | 71/98 |

*Primary Examiner*—Glennon H. Hollrah
*Attorney, Agent, or Firm*—Hammond & Littell

[57] ABSTRACT

Novel urea derivatives of the formula

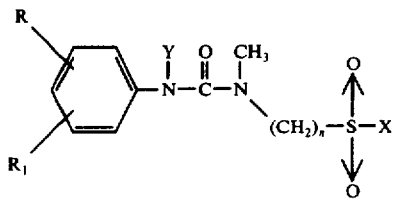

I wherein R and $R_1$ are individually selected from the group consisting of hydrogen, chlorine, bromine, nitro, trifluoromethyl, lower alkyl of 1 to 6 carbon atoms and lower alkoxy of 1 to 6 carbon atoms, $n$ is 0 or 1, X is selected from the group consisting of lower alkyl of 1 to 6 carbon atoms optionally substituted with halogen and a nitrogen heterocyclic optionally containing 1 or more other heteroatoms, Y is selected from the group consisting of hydrogen, alkyl of 1 to 4 carbon atoms and S—Z wherein Z is a nitrogen heterocyclic optionally containing 1 or more other heteroatoms and the dotted lines indicate that the compound of formula I may contain no oxygen bound to the sulfur atom or may be in sulfoxide or sulfonyl form which are useful as herbicides and thereon preparation.

12 Claims, No Drawings

SUBSTITUTED UREAS AS HERBICIDES

PRIOR APPLICATIONS

This application is a continuation-in-part of our co-pending, commonly assigned patent application Ser. No. 582,877 filed June 2, 1975, now abandoned, which in turn is a continuation of patent application Ser. No. 305,336 filed Nov. 10, 1972, now abandoned.

STATE OF THE ART

French patent No. 2,065,315 describes the use of N-(2-fluorophenyl)-N'-substituted ureas as herbicides and West German published application Ser. No. 1,910,490 describes the use of N-aryl-N'-alkyl-N'-arylthio-ureas as herbicides.

U.S. Pat. Nos. 3,165,549, 3,288,586 and 3,228,762 also disclose various urea compounds as herbicides.

OBJECTS OF THE INVENTION

It is an object of the invention to provide the novel substituted ureas of formula I and their preparation.

It is another object of the invention to provide novel herbicidal compositions.

It is a further object of the invention to provide a novel method of killing weeds, particularly in cereal crops.

These and other objects and advantages of the invention will become obvious from the following detailed description.

THE INVENTION

The novel substituted ureas of the invention have the formula

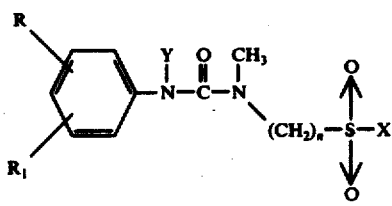

wherein R and $R_1$ are individually selected from the group consisting of hydrogen, chlorine, bromine, nitro, trifluoromethyl, lower alkyl of 1 to 6 carbon atoms and lower alkoxy of 1 to 6 carbon atoms, $n$ is 0 or 1, X is selected from the group consisting of lower alkyl of 1 to 6 carbon atoms optionally substituted with halogen and a nitrogen heterocyclic optionally containing 1 or more other heteroatoms, Y is selected from the group consisting of hydrogen, alkyl of 1 to 4 carbon atoms and S—Z wherein Z is a nitrogen heterocyclic optionally containing 1 or more other heteroatoms and the dotted lines indicate that the compound of formula I may contain no oxygen bound to the sulfur atom or may be in sulfoxide or sulfonyl form.

Among the preferred compounds are those wherein X is lower alkyl such as methyl, ethyl, propyl, isopropyl, n-butyl, sec-butyl or tert.-butyl or halo substituted lower alkyl such as chloromethyl or a heterocyclic of 5 to 6 ring atoms such as morpholino, pyridino, pyrrolidino, etc. The most preferred compounds are N-methyl-N-ethylthio-N'-(3,4-dichlorophenyl)-urea, N-methyl-N-ethylthio-N'-(3-trifluoromethylphenyl)-urea, N-methyl-N-ethylthio-N'-(3-chloro-4-methylphenyl)-urea, N-methyl-N-ethylthio-N'-(3-chloro-4-methoxyphenyl)-urea and N-methyl-N-ethylthio-N'-(4-bromophenyl)-urea.

A novel process of the invention for the preparation of ureas of formula I wherein Y is hydrogen and R, $R_1$, X and $n$ have the above definition comprises condensing in the presence of a tertiary base a urea of the formula

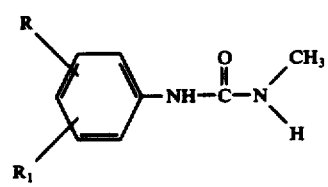

with a chloride of the formula $$Cl-(CH_2)_n-S-X \qquad III$$

wherein R, $R_1$, X and $n$ have the above definitions to form a compound of the formula

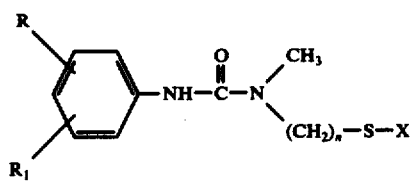

which can be reacted with 1 to 2 moles of an oxidation agent to form the corresponding sulfoxide or sulfonyl compound, respectively.

The preferred tertiary base is pyridine or triethylamine. The oxidation agent may be potassium permanganate, peracetic acid, perbenzoic acid, m-chloroperbenzoic acid, hydrogen peroxide, perphthalic acid, chromic anhydride, manganese dioxide or sodium periodate. In the case of the sulfone formation which requires 2 moles of the oxidation agent, it may be necessary to heat the reaction mixture so that the reaction will not stop at the sulfoxide stage in spite of excess oxidation agent.

Another process for the preparation of the compounds of formula I wherein Y is hydrogen and R, $R_1$, X and $n$ have the above definitions comprises reacting an isocyanate of the formula

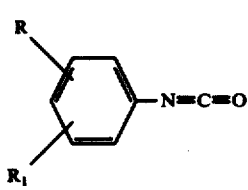

with a sulfenamide of the formula

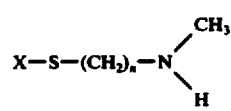

to obtain a compound of formula Ia which may be oxidized to the sulfoxide or sulfonyl compound as before. The said isocyanate condensation is preferably effected in the presence of a small amount of a tertiary base such as pyridine or triethylamine.

A process for the preparation of sulfonyl compounds of formula I where R, $R_1$ and X have the above definition and n is 0 and Y is hydrogen comprises condensing an isocyanate of formula IV with a compound of the formula

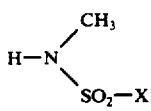

VI to form a compound of the formula

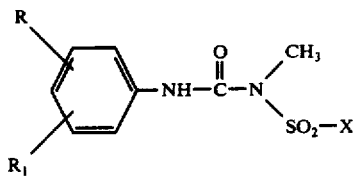

Ib

The said condensation is preferably effected in an organic solvent such as ether, isopropyl ether or tetrahydrofuran.

A process for the preparation of a sulfonyl compound of formula I wherein n is 0 and Y is hydrogen and R, $R_1$ and X have the above definition comprises reacting an amine of the formula

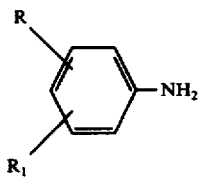

VII with a compound of the formula

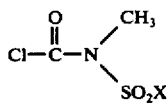

VIII to obtain a compound of formula Ib. The condensation is effected in the presence of a tertiary base such as triethylamine or pyridine in an organic solvent such as ether, isopropyl ether or tetrahydrofuran.

A process for the preparation of compounds of formula I whose sulfur is not oxidized and wherein n is 0, Y is alkyl of 1 to 4 carbon atoms and R, $R_1$ and X have the above definitions comprises reacting a compound of the formula

IX

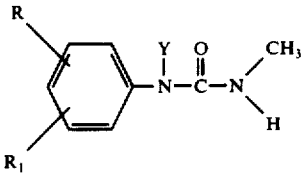

with a chloride of the formula Cl—S—X.

A process for the preparation of a compound of formula I wherein the sulfur is not oxidized and R, $R_1$ and X have the above definitions, n is 0 and Y is S—Z and Z is a heterocyclic as defined above comprises reacting a compound of the formula

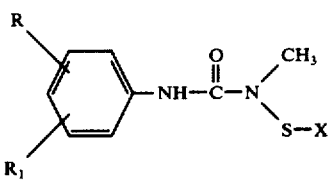

X with a compound of the formula Cl—Y to form the corresponding compound of formula I.

The novel herbicidal compositions of the invention are comprised of an effective amount of at least one compound of formula I and an inert carrier. The compositions may also contain one or more other pesticides or one or more other products to influence the growth of plants.

The said compositions may be in the form of powders, granules, suspensions, emulsions or solutions containing the active ingredient such as a mixture with a vehicle and/or an anionic, cationic or nonionic surface active agent assuring, with others, a uniform dispersion of the substances of the composition. The vehicle used may be a liquid such as water, alcohol, hydrocarbons or other organic solvents, animal, vegetable or mineral oils or a powder such as talc, clays, silicates or keiselguhr. The compositions generally contain 5 to 90%, preferably 10 to 50%, by weight of the active ingredient.

An example of useful herbicidal composition in the form of a wettable powder consists of 25% by weight of N-methyl-N-ethylthio-N'-(3-chloro-4-methylphenyl)-urea or N-methyl-N-ethylthio-N'-(3,4-dichlorophenyl)-urea, 15% by weight of Ekapersol S (condensation product of sodium naphthalenesulfonate), 0.5% by weight of Brecolane NVA (sodium alkylnaphthalenesulfonate), 34.5% by weight of Zeosil 39 (precipitated synthetic hydrated silica) and 25% by weight of Vercoryl S (Colloidal Kaolin).

The remarkable herbicidal properties of the compounds of formula I make them useful in agriculture for combatting harmful organisms and particularly undesired weeds. The herbicidal properties have been demonstrated by tests on plants of large botanical families as reported herein.

The novel method of the invention of combatting weeds comprises contacting the weeds either pre-emergence or post-emergence with a herbicidally effective amount of at least one compound of formula I. The usual effective dose is 0,625 to 5 K/ha when applied post-emergence and pre-emergence.

The starting materials for the processes of the invention are either known or can be prepared by known processes. The ureas of formula II, for example, can be prepared by condensation of methyl isocyanate with an aniline of the formula

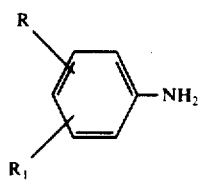

N-methyl-N'-(4-bromophenyl)-urea is described by Toshio et al [Agr. Biol. Chem., Vol. 33 (1969), p. 785] and N-methyl-N'-(3-trifluoromethylphenyl)-urea is described in British patent No. 923,670 while N-methyl-N'-(3,4-dichlorophenyl)-urea is described by Onley et al. [J. Ass. Off. Anal. Chem., Vol. 52 (1969), p. 545].

The compounds of formula II may also be prepared by acid hydrolysis of a compound of the formula

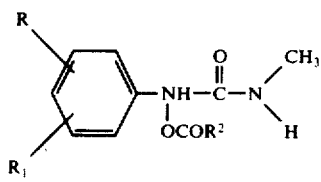

wherein $R_2$ is lower alkyl. N-methyl-N'-(3-chloro-4-methylphenyl)-urea described by Svirskaya [Zh. Org. Khim., Vol. 5 (2) (1969), p. 272], can be prepared with this method.

3,4-dichlorophenyl isocyanate can be prepared by condensation of 3,4-dichloroaniline with phosgene as described by Beaver et al. [J.A.C.S., Vol. 79 (1957), p. 1236] and other phenyl isocyanates of formula IV can be prepared in an analogous manner.

The preparation of the alkyl sulfenyl chlorides of formula III may be prepared by reaction of chlorine with dialkyl disulfide as described by Noth et al. [Ber., Vol. 94 (1961), p. 634] for the preparation of methyl sulfenyl chloride.

Compounds of the formula

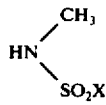

can be prepared by condensation of methylamine and sulfonic acid chlorides of the formula $XSO_2Cl$. The preparation of N-methyl-N-methylsulfonylamine is described by Helferich et al. [Ber., Vol. 73 B, (1940), p. 1131].

N-methyl-N-methylsulfonyl-carbamoyl chloride may be prepared by reacting phosgene and the sodium salt of N-methyl-N-methylsulfonylamine described in West German patent No. 951,719 and other chlorides of this type can be prepared in an analogous manner. One of these chlorides not described in the literature is N-methyl-N-(methylsulfonyl)-carbamoyl chloride.

Compounds of the formula

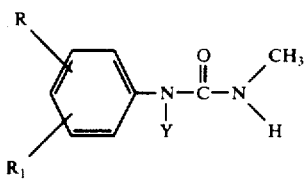

wherein Y is alkyl of 1 to 4 carbon atoms may be prepared by reaction of methyl isocyanate with the corresponding N-alkyl-aniline.

Compounds of the formula

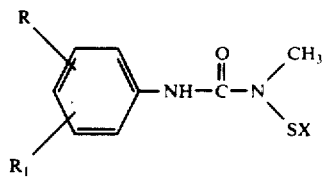

may be prepared by reacting a chloride of the formula ClSX with a urea of the formula

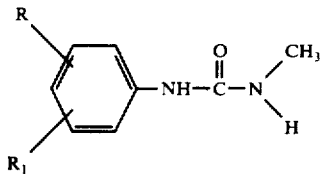

N-chloromercaptomorpholine is described by Levchenko et al. [Zh. Org. Khim., Vol. 5 (8) (1969), p. 1516].

Tert.-butyl mercaptomonomethylamide may be prepared by reacting mercury di-(tert.-butanethiolate) with first iodine and then monomethylamine as described by Rheinboltd et al. [Ber., Vol. 72 (1939), p. 657]. Other sulfenamides of the formula

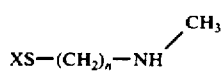

can be prepared in an analogous manner.

In the following examples there are described several preferred embodiments to illustrate the invention. However, it should be understood that the invention is not intended to be limited to the specific embodiments.

EXAMPLE 1

N-METHYL-N-TERT.-BUTYLTHIO-N'-(3,4-DICHLOROPHENYL)-UREA 12 g of tert.-butylmercapto monomethylamine, 20 g of 3,4-dichlorophenyl isocyanate and 3 drops of triethylamine were added to 120 ml of tetrahydrofuran and after stirring the mixture for 30 minutes, the solvent was distilled off under reduced pressure. The residue was crystallized from ethanol to obtain 25.6 g of N-methyl-N-tert.-butylthio-N'-(3,4-dichlorophenyl)-urea melting at 127° C.

Analysis: $C_{12}H_{16}Cl_2N_2OS$; molecular weight = 307.24; Calculated: %C, 46.91; %H, 5.25; %Cl, 23.08; %N, 9.12; %S, 10.43; Found: %C, 47.3; %H, 5.4; %Cl, 22.7; %N, 9.0; %S, 10.3.

EXAMPLE 2

N-METHYL-N-TERT.-BUTYLSULFINYL-N'-(3,4-DICHLOROPHENYL)-UREA 4.3 g of 80% m-chloroperbenzoic acid dissolved in 50 ml of methylene chloride were added dropwise to a solution of 6.15 g of N-methyl-N-tert.-butylthio-N'-(3,4-dichlorophenyl)-urea in 60 ml of methylene chloride cooled to 0° C and after stirring the mixture at 0° C for 20 minutes, the insolubles were removed by filtration. The organic phase was washed with an aqueous saturated solution of sodium bicarbonate, then with water and dried. The solvent was distilled off under reduced pressure and the residue was crystallized from isopropyl ether to obtain 5.5 g of N-methyl-N-tert.-butylsulfinyl-N'-(3,4-dichlorophenyl)-urea melting at 118° C.

Analysis: $C_{12}H_{16}Cl_2N_2O_2S$; molecular weight = 323.24; Calculated: %C, 44.59; %H, 4.99; %Cl, 21.93; %N, 8.67; %S, 9.92; Found: %C, 44.6; %H, 4.8; %Cl, 21.8; %N, 8.8; %S, 10.1.

EXAMPLE 3

N-METHYL-N-TERT.-BUTYLSULFONYL-N'-(3,4-DICHLOROPHENYL)-UREA 9.2 g of 80% m-chloroperbenzoic acid were added portion wise to 6.15 g of N-methyl-N-tert.-butylthio-N'-(3,4-dichlorophenyl)-urea in 60 ml of methylene chloride and the resulting mixture was refluxed for 30 minutes. After cooling to 0° C, the insolubles were removed by filtration and the organic phase was washed with an aqueous saturated solution of sodium bicarbonate, then with water and dried. The solvent was distilled off under reduced pressure and the residue was crystallized from ethanol to obtain 5.40 g of N-methyl-N-tert.-butylsulfonyl-N'-(3,4-dichlorophenyl)-urea melting at 116° C.

Analysis: $C_{12}H_{16}Cl_2N_2O_3S$; molecular weight = 339.24; Calculated: %C, 42.49; %H, 4.75; %Cl, 20.90, %N, 8.25; %S, 9.45; Found: %C, 42.7; %H, 4.7; %Cl, 20.7; %N, 8.2; %S, 9.7.

EXAMPLE 4

N-METHYL-N-MORPHOLINOTHIO-N'-(3,4-DICHLOROPHENYL)-UREA

STEP A: N-methyl-N'-(3,4-dichlorophenyl)-urea

A mixture of 27.4 g of 3,4-dichloroaniline in 140 ml of isopropyl ether was added slowly to 9 g of methyl isocyanate in 100 ml of isopropyl ether and the mixture was refluxed for 2 hours and was then cooled to 0° C. The precipitate formed was recovered by vacuum filtration and was washed with isopropyl ether. The mother liquors were concentrated to obtain a second crop. The two combined crops weighing 19.5 g and melting at 156° C were crystallized from ethyl acetate to obtain N-methyl-N'-(3,4-dichlorophenyl)-urea melting at 160° C, identical to the product described by Onley et al., J. Ass. Off. Anal. Chem., Vol. 52 (1969), p. 545.

Analysis: $C_8H_8Cl_2N_2O$; molecular weight = 219.07; Calculated: %C, 43.86; %H, 3.68; %Cl, 32.37; %N, 12.79; Found: %C, 43.7; %H, 3.6; %Cl, 32.4; %N, 12.7.

STEP B: N-methyl-N-morpholinothio-N'-(3,4-dichlorophenyl) urea 43.8 g of N-methyl-N'-(3,4-dichlorophenyl)-urea and 21.1 g of triethylamine were added to 440 ml of tetrahydrofuran and the mixture was stirred until dissolution occurred. A solution of 36 g of N-chloro-mercaptomorpholine in 60 ml of tetrahydrofuran was added in 5 minutes to the said solution and the mixture was stirred for 4 hours at room temperature. The precipitate formed was removed by filtration and the filtrate was concentrated to dryness under reduced pressure. The residue was crystallized from ethyl acetate to obtain 42.5 g of N-methyl-N-morpholinothio-N'-(3,4-dichlorophenyl)-urea melting at 142° C.

Analysis: $C_{12}H_{15}Cl_2N_3O_2S$; molecular weight = 336.246; Calculated: %C, 42.86; %H, 4.50; %Cl, 21.09; %N, 12.50; %S, 9.54; Found: %C, 42.8; %H, 4.8; %Cl, 21.0; %N, 12.4; %S, 9.6.

EXAMPLE 5

N-METHYL-METHYLTHIO-N'-(3,4-DICHLOROPHENYL)-UREA

A mixture of 20 ml of methylsulfenyl chloride and 200ml of ethyl ether was added slowly while keeping the temperature below −30° C to a solution of 40 g of N-methyl-N'-(3,4-dichlorophenyl)-urea in 500 ml of pyridine and the mixture was stirred for 1 hour at −30° C. After letting the temperature rise to 5° C, the mixture was stirred for 17 hours and the mixture was poured into a mixture of ice and water. The mixture was extracted with methylene chloride and the methylene chloride extract was washed with water and dried. The volatile fractions were removed by distillation under reduced pressure and the residue was crystallized from isopropyl ether to obtain 29.4 g of N-methyl-N-methylthio-N'-(3,4-dichlorophenyl)-urea melting at 93° C. A microanalytical sample was obtained by chromatography over silica gel and elution with a 9-1 benzene-ethyl acetate mixture.

Analysis: $C_9H_{10}Cl_2N_2OS$; molecular weight = 265.16; Calculated: %C, 40.76; %H, 3.79; %Cl, 26.75; %N, 10.56; %S, 12.10; Found: %C, 40.6; %H, 3.8; %Cl, 26.8; %N, 10.5; %S, 12.0.

EXAMPLE 6

N-METHYL-N-ETHYLTHIO-N'-(3,4-DICHLOROPHENYL)-UREA

A solution of 67 g of sulfuryl chloride in 100 ml of methylene chloride was added dropwise to a solution of 61 g of diethyldisulfide in 600 ml of methylene chloride cooled to −40° C and after the temperature was raised to −5° C, the mixture was stirred for 5 minutes. The mixture was cooled to −40° C and a solution of 57 g of N-methyl-N'-(3,4-dichlorophenyl)-urea in 460 ml of pyridine was added dropwise thereto. The mixture was stirred at −40° C for 1 hour and for another hour at −20° C. The mixture was poured into an icewater mixture and the pH was adjusted to 3.5 by addition of concentrated hydrochloric acid. The organic phase was decanted and the aqueous phase was extracted with methylene chloride. The combined organic phases were washed with water, dried and evaporated to dryness under reduced pressure. The residue was crystallized from isopropyl ether and subjected to chromatography over silica gel. Elution with a 7-3 benzene-ethyl acetate mixture gave 22 g of N-methyl-N-ethylthio-N'-(3,4-dichlorophenyl)-urea melting at 71° C.

Analysis: $C_{10}H_{12}Cl_2N_2OS$; molecular weight = 279.16; Calculated: %C, 43.02; %H, 4.34; %Cl, 25.41; %N, 10.04; %S, 11.48; Found: %C, 43.2; %H, 4.4; %Cl, 25.2; %N, 10.1; %S, 11.1.

EXAMPLE 7

N-METHYL-N-(2-THIAPROPYL)-N'-(3,4-DICHLOROPHENYL)-UREA 11 g of N-methyl-N'-(3,4-dichlorophenyl)-urea, 60 g of potassium carbonate and 50 ml of dimethylsulfur chloride were added at 10° C to 150 ml of dimethylsulfoxide and the mixture was allowed to stand until exothermic generation of heat ceased. The reaction mixture was added to water and was extracted with ether. The ether solution was washed with water, dried and concentrated to dryness by distillation under reduced pressure. The residue was crystallized from isopropyl ether and then ethyl acetate to obtain 7.7 g of N-methyl-N-(2-thiapropyl)-N'-(3,4-dichlorophenyl)-urea melting at 103° C.

EXAMPLE 8

N-METHYL-N-METHYLSULFONYLMETHYL-N'-(3,4-DICHLOROPHENYL)-UREA

A solution of 27 g of N-methyl-N-(2-thiapropyl)-N'-(3,4-dichlorophenyl)-urea in 250 ml of methylene chloride was added at 10° C to a solution of 34.5 g of m-chloroperbenzoic acid in 520 ml of methylene chloride and the mixture was stirred at room temperature for 3 ½ hours. The precipitate was filtered off and the filtrate was distilled to dryness under reduced pressure. The residue was dissolved in ethyl acetate and the m-chlorobenzoic acid formed was removed by filtration. The organic filtrate was washed with aqueous 5% sodium bicarbonate solution, then with water, dried and concentrated to dryness under reduced pressure. The residue was subjected to chromatography over silica gel and was eluted with ethyl acetate and crystallized from isopropyl ether to obtain 11 g of N-methyl-N-(methylsulfonylmethyl)-N'-(3,4-dichlorophenyl)-urea melting at 159° C. A microanalytical sample was obtained by crystallization from ethyl acetate.

Analysis: $C_{10}H_{12}Cl_2N_2O_3S$; molecular weight = 311.188; Calculated: %C, 38.60; %H, 3.89; %Cl, 22.79; %N, 9.00; %S, 10.30; Found: %C, 38.8; %H, 3.9; %Cl, 22.5; %N, 9.1; %S, 10.6.

EXAMPLE 9

N-METHYL-N-ETHYLTHIO-N'-(3-CHLORO-4-METHOXYPHENYL)-UREA

A mixture of 67 g of sulfuryl chloride and 100 ml of methylene chloride was slowly added at −40° C to 68 g of diethyl disulfide in 600 ml of methylene chloride and after the temperature was slowly raised to −5° C, the mixture was stirred at −5° C for 5 minutes. The mixture was then cooled to −40° C and a solution of 56 g of N-methyl-N'-(3-chloro-4-methoxyphenyl)-urea in 800 ml of pyridine was added thereto. The mixture was stirred at −20° C for 2 hours and was then added to a water-ice mixture. The pH of the mixture was adjusted to 5 by addition of an aqueous concentrated solution of hydrochloric acid and was extracted with methylene chloride. The combined organic extracts were washed with water until the wash water was neutral, then dried and distilled to dryness under reduced pressure. The residue was chromatographed over silica gel and eluted with a 7-3 benzene-ethyl acetate mixture. The product was crystallized from isopropyl ether to obtain 23.5 g of N-methyl-N-ethylthio-N'-(3-chloro-4-methoxyphenyl)-urea melting at 60° C.

Analysis: $C_{11}H_{15}Cl N_2O_2S$; molecular weight = 274.76; Calculated: %C, 48.09; %H, 5.50; %Cl, 12.90; %N, 10.20; %S, 11.67; Found: %C, 47.9; %H, 5.2; %Cl, 13.0; %N, 10.3; %S, 11.8.

EXAMPLE 10

N-METHYL-N-ETHYLTHIO-N'-(3-CHLORO-4-METHYLPHENYL) UREA

Ethane sulfenyl chloride was prepared extemporaneously as in Example 9 from 68 g of diethyl disulfide and 67 g of sulfuryl chloride, cooled to −40° C and a solution of 51.5 g of N-methyl-N'-(3-chloro-4-methylphenyl)-urea in 800 ml of pyridine were added thereto. The mixture was allowed to come to a temperature of −20° C and was stirred for 1½ hours at −20° C. The mixture was poured into a water-ice-hydrochloric acid mixture and was then extracted with methylene chloride. The organic phase was washed with water, dried and concentrated to dryness under reduced pressure and the residue was chromatographed over silica gel. The product was eluted with a 9-1 benzene-ethyl acetate mixture and the product was dissolved in ethyl ether. The ether solution was treated with activated carbon, filtered, and concentrated to dryness to obtain 19.5 g of N-methyl-N-ethylthio-N'-(3-chloro-4-methylphenyl)-urea melting at <50° C.

Analysis: $C_{11}H_{15}Cl N_2OS$; molecular weight = 258.77; Calculated: %C, 51.06; %H, 5.84; %Cl, 13.70; %N, 10.83; %S, 12.39; Found: %C, 50.9; %H, 5.9; %Cl, 13.4; %N, 10.6; %S, 12.6.

EXAMPLE 11

N-METHYL-N-ETHYLTHIO-N'-(3-TRIFLUOROMETHYLPHENYL)-UREA

Ethane sulfenyl chloride was prepared extemporaneously as in Example 9 from 68 g of diethyldisulfide and 67 g of sulfuryl chloride, cooled to −40° C and then a solution of 57 g of N-methyl-N'-(3-trifluoromethylphenyl)-urea in 800 ml of pyridine was added thereto. The mixture was stirred at −40° C for 30 minutes and after letting the temperature rise to −20° C, the mixture was stirred at −20° C for 1½ hours. The mixture was added to a mixture of water, ice and hydrochloric acid and was extracted with methylene chloride. The organic phase was washed with water, dried and evaporated to dryness. The residue was chromatographed over silica gel and eluted with a 9-1 benzene-ethyl acetate mixture. Rectification under reduced pressure resulted in 21 g of N-methyl-N-ethylthio-N'-(3-trifluoromethylphenyl)-urea boiling at 126° C under 0.8 mm Hg and having a refractive index $N_D^{22}$ = 1.5200.

Analysis: $C_{11}H_{13}F_3N_2OS$; molecular weight = 278.3; Calculated: %C, 47.47; %H, 4.71; %F, 20.48; %N, 10.07; %S, 11.52; Found: %C, 47.7; %H, 4.8; %F, 20.7; %N, 9.8; %S, 11.7.

EXAMPLE 12

N-METHYL-N-ETHYLTHIO-N'-(4-BROMOPHENYL)-UREA

Ethane sulfneyl chloride was prepared as in Example 9 from 68 g of diethyldisulfide and 67 g of sulfuryl chloride, cooled to −40° C and a solution of 60 g of N-methyl-N'-(4-bromophenyl)-urea in 800 ml of pyridine was added thereto. After stirring the reaction mixture for 30 minutes at −40° C, the temperature was allowed to rise to −20° C and the mixture was stirred for 1½ hours at this temperature. The mixture was poured into a mixture of water, ice and hydrochloric acid and was extracted with methylene chloride. The organic phase was washed with water, dried and evaporated to dryness under reduced pressure. The residue was chromatographed over silica gel and eluted with a 7-3 benzene-ethyl acetate mixture. The product was dissolved in ethyl ether and the solution was treated with activated carbon, filtered and concentrated to dryness under reduced pressure. The residue was added to petroleum ether (b.p. = 65°-75° C) and the precipitate formed was recovered by vacuum filtration to obtain 33 g of N-methyl-N-ethylthio-N'-(4-bromophenyl)-urea melting at <50° C.

Analysis: $C_{10}H_{13}Br\ N_2OS$; molecular weight = 289.20; Calculated: %C, 41.53; %H, 4.53; %Br, 27.63; %N, 9.68; %S, 11.09; Found: %C, 41.7; %H, 4.7; %Br, 27.3; %N, 9.4; %S, 10.8.

EXAMPLE 13

N-METHYL-N-(4-MORPHOLINOTHIO)-N'-(3-CHLORO-4-METHOXYPHENYL)-UREA

A solution of 33.8 g of N-chloro-mercaptomorpholine in 50 ml of tetrahydrofuran was slowly added to 43 g of N-methyl-N'-(3-chloro-4-methoxyphenyl)-urea in 400 ml of tetrahydrofuran and 20.2 g of triethylamine and after stirring for 16 hours at 20° C, the mixture was poured into water. The mixture was extracted with ethyl acetate and the organic phase was washed with water and concentrated to dryness under reduced pressure. The residue was chromatographed over silica gel and eluted with a 9-1 chloroform-acetate mixture. The product was added to isopropyl ether and the precipitate formed was recovered by vacuum filtration to obtain 38 g of N-methyl-N-(4-morpholinothio)-N'-(3-chloro-4-methoxyphenyl)-urea melting at 136° C.

Analysis: $C_{13}H_{18}Cl\ N_3O_3S$; molecular weight = 331.82; Calculated: %C, 47.05; %H, 5.47; %Cl, 10.69; %N, 12.66; %S, 9.67; Found: %C, 46.7; %H, 5.4; %Cl, 10.8; %N, 12.6; %S, 9.6.

EXAMPLE 14

N-METHYL-N-(4-MORPHOLINOTHIO)-N'-(3-CHLORO-4-METHYLPHENYL)-UREA

A solution of 33.8 g of N-chloro-mercaptomorpholine in 50 ml of tetrahydrofuran was slowly added to 40 g of N-methyl-N'-(3-chloro-4-methylphenyl)-urea in 400 ml of tetrahydrofuran and 20.2 g of triethylamine and after stirring for 16 hours at 20° C, the mixture was poured into water and extracted with ethyl acetate. The organic phase was washed with water, dried and evaporated to dryness under reduced pressure and the residue was chromatographed over silica gel and eluted with a 9-1 chloroform-acetone mixture. The product was added to isopropyl ether and was vacuum filtered to obtain 22 g of N-methyl-N-(4-morpholinothio)-N'-(3-chloro-4-methylphenyl)-urea melting at 158° C.

Analysis: $C_{13}H_{18}Cl\ N_3O_2S$; molecular weight = 315.82; Calculated: %C, 49.43; %H, 5.75; %Cl, 11.22; %N, 13.30; %S, 10.16; Found: %C, 49.4; %H, 5.6; %Cl, 11.5; %N, 13.6; %S, 10.5.

EXAMPLE 15

N-METHYL-N-(4-MORPHOLINOTHIO)-N'-(3-TRIFLUOROMETHYLPHENYL)-UREA

A solution of 33.8 g of N-chloro-mercaptomorpholine in 50 ml of tetrahydrofuran was slowly added to 43.6 g of N-methyl-N'-(3-trifluoromethylphenyl)-urea in 400 ml of tetrahydrofuran and 20.2 g of triethylamine, and after stirring for 16 hours at 20° C. the mixture was poured into water and extracted with ethyl acetate. The organic phase was washed with water, dried and evaporated to dryness under reduced pressure. The residue was chromatographed over silica gel and eluted with a 7-3 benzene-ethyl acetate mixture. The product was added to isopropyl ether and the precipitate formed was recovered by vacuum filtration and was washed and dried to obtain 33 g of N-methyl-N-(4-morpholinothio)-N'-(3-trifluoromethylphenyl)-urea melting at 128° C.

Analysis: $C_{13}H_{16}F_3N_3O_2S$; molecular weight = 335.35; Calculated: %C, 46.56; %H, 4.81; %F, 16.99; %N, 12.53; %S, 9.56; Found: %C, 46.7; %H, 4.8; %F, 17.3; %N, 12.3; %S, 9.3.

EXAMPLE 16

N-METHYL-N-(4-MORPHOLINOTHIO)-N'-(4-BROMOPHENYL)-UREA

A solution of 33.8 g of N-chloro-mercaptomorpholine in 50 ml of tetrahydrofuran was slowly added to 46 g of N-methyl-N'-(4 bromophenyl)-urea in 450 ml of tetrahydrofuran and 20.2 g of triethylamine and after stirring for 16 hours at 20° C, the mixture was poured into water and extracted with ethyl acetate. The organic phase was washed with water, dried and concentrated to dryness under reduced pressure. The residue was chromatographed over silica gel and eluted with a 9-1 chloroform-acetone mixture. The product was added to isopropyl ether and the precipitate formed was recovered by vacuum filtration and was washed and dried to obtain 31.5 g of N-methyl-N-(4-morpholinothio)-N'-(4-bromophenyl)-urea melting at 144° C.

Analysis: $C_{12}H_{16}BrN_3O_2S$; molecular weight = 346.25; Calculated: %C, 41.62; %H, 4.66; %Br, 23.08; %N, 12.14; %S, 9.26; Found: %C, 41.6, %H, 4.7; %Br, 22.8; N, 12.3; %S, 9.0.

EXAMPLE 17

N-PROPYLTHIO-N-METHYL-N'-(3,4-DICHLOROPHENYL)-UREA 13,4 g of sulfuryl chloride were slowly added at −30° C to a mixture of 106 ml of methylene chloride and 15 g of dipropyldisulfide, and after the temperature rose to −10°C, the mixture was stirred for 10 minutes at −10° C to obtain a solution of propyl sulfenyl chloride. The solution was cooled to −30° C and solution of 22 g of N-methyl-N'-(3,4-dichlorophenyl)-urea in 140 ml of pyridine was added thereto. The mixture was stirred for 5 hours at −20° C, then for 17 hours at 0° C. The mixture was poured into a water-ice-hydrochloric acid-methylene chloride mixture, was stirred and decanted. The organic phase was washed with water, dried and concentrated to dryness under reduced pressure. The residue was chromatographed over silica gel and eluted with a 9-1 benzene-ethyl acetate mixture. The product was added to petroleum ether (b.p. = 65°-75° C) and the precipitate formed was recovered by vacuum filtration and was washed and dried to obtain 14 g of N-methyl-N-propylthio-N'-(3,4-dichlorophenyl)-urea melting at 40° C.

Analysis: $C_{11}H_{14}Cl_2N_2OS$; molecular weight = 293.22; Calculated: %C, 45.06; %H, 4.81; %Cl, 24.18; %N, 9.55; %S, 10.93; Found: %C, 45.4; %H, 5.0; %Cl, 23.9; %N, 9.8; %S, 11.2.

EXAMPLE 18

N-METHYL-N-ISOPROPYLTHIO-N'-(3,4-DICHLOROPHENYL)-UREA 40.5 g of sulfuryl chloride were slowly added at −30° C to 45 g of diisopropyldisulfide and 320 ml of methylene chloride, and after raising the temperature to −10° C, the mixture was stirred at this temperature for 10 minutes. A solution of 66 g of N-methyl-N'-(dichlorophenyl)-urea in 420 ml of pyridine was slowly added at −30° C to the said solution of isopropyl sulfenyl chloride formed above and the mixture was stirred for 5 hours at −20° C and then for 17 hours at 0° C. The mixture was added to a water-methylene chloride-hydrochloric acid mixture and was stirred and decanted. The organic phase was washed with water, dried and concentrated to dryness under reduced pressure. The residue was chromatographed over silica gel and was eluted with a 9-1 benzene-ethyl acetate mixture. The product was added to isopropyl ether and the precipitate formed was recovered by vacuum filtration and was washed and dried to obtain 21.5 g of N-methyl-N-isopropylthio-N'-(3,4-dichlorophenyl)-urea melting at 65° C.

Analysis: $C_{11}H_{14}Cl_2N_2OS$; molecular weight = 293.22; Calculated: %C, 45.06; %H, 4.81; %Cl, 24.18; %N, 9.55; %S, 10.93; Found: %C, 45.3; %H, 4.9; %Cl, 24.0; %N, 9.7; %S, 11.1.

EXAMPLE 19

N-METHYL-N-n-BUTYLTHIO-N'-(3,4-DICHLOROPHENYL)-UREA 26.8 g of sulfuryl chloride were slowly added at −30° C to 35.6 g of dibutyl disulfide and 212 ml of methylene chloride and after raising the temperature to −10° c, the mixture was stirred for 10 minutes at −10° C to obtain a solution of n-butyl sulfenyl chloride. A solution of 44 g of N-methyl-N'-(3,4-dichlorophenyl)-urea in 280 ml of pyridine was added slowly to the said solution at −30° C and the mixture was stirred at −20° C for 5 hours, then at 0° C for 17 hours and poured into a methylene chloride-water-ice-hydrochloric acid mixture. The mixture was stirred and decanted and the organic phase was washed with water, dried and concentrated to dryness under reduced pressure. The residue was crystallized from methanol to obtain 22.1 g of N-methyl-N-n-butylthio-N'-(3,4-dichlorophenyl)-urea melting at 47° C.

Analysis: $C_{12}H_{16}Cl_2N_2OS$; molecular weight = 307.25; Calculated: %C, 46.91; %H, 5.25; %Cl, 23.08; %N, 9.12; %S, 10.44; Found: %C, 47.1; %H, 5.5; %Cl, 23.0 %N, 8.7; %S, 10.7.

EXAMPLE 20

N-METHYL-N-METHYLSULFONYL-N'-(3,4-DICHLOROPHENYL)-UREA

STEP A: N-methyl-N-methylsulfonyl-carbamoyl chloride 95 g of N-methylsulfonyl-N-methylamine were added to a solution of 36.2 g of sodium hydroxide in 300 ml of methanol and after stirring at 20° C for two hours, the methanol was distilled off under reduced pressure. The residue was added to isopropyl ether and the precipitate formed was recovered by vacuum filtration to obtain 115 g of the sodium salt of N-methylsulfonyl-N-methylamine. The said salt was added at 5° C to a solution of 300 g of phosgene in 1000 ml of toluene and after stirring for 3 hours at 5° C, the mixture stood overnight at 5° C. The precipitate formed was filtered off and the filtrate was evaporated to dryness under reduced pressure. The residue was added to petroleum ether (b.p. = 65°-75° C) and the precipitate formed was recovered by vacuum filtration and was dried to obtain 77 g of N-methyl-sulfonyl-N-methyl carbamoyl chloride.

A solution of 16 g of N-methylsulfonyl-N-methyl-carbamoyl chloride in 100 ml of tetrahydrofuran was slowly added at less than 10° C to a mixture of 150 ml of tetrahydrofuran, 9.4 g of triethylamine and 15 g of 3,4-dichloroaniline and after stirring for 3 hours, the insolubles were removed by filtration, and the filtrate was concentrated to dryness under reduced pressure to obtain 16 g of N-methyl-N-methylsulfonyl-N'-(3,4-dichlorophenyl)-urea melting at 140° C. Crystallization from ethanol gave an unchanged melting point.

Analysis: $C_9H_{10}Cl_2N_2O_3S$; molecular weight = 297.16; Calculated: %C, 36.37; %H, 3.41; %Cl, 23.86; %N, 9.42; %S, 10.76; Found: %C, 36.4; %H, 3.5; %Cl, 23.5; %N, 9.6; %S, 10.8.

EXAMPLE 21

N-METHYL-N-CHLOROMETHYLSULFONYL-N'-(3,4-DICHLOROPHENYL)-UREA

A solution of 19 g of 3,4-dichlorophenyl isocyanate in 150 ml of ethyl ether was added to a solution of 14.4 g of N-methyl-N-chloromethylsulfonyl-amine in 150 ml of ethyl ether and after the addition of 0.1 ml of triethylamine, the mixture was stirred for a hour at 20° C. The crystals formed were recovered by vacuum filtration, were washed, dried and dissolved in chloroform. The insolubles were removed by filtration and the filtrate was concentrated to dryness. The product was crystallized from methyl ethyl to obtain 21.3 g of N-methyl-N-chloromethylsulfonyl-N'-(3,4-dichlorophenyl)-urea melting at 119° C.

Analysis: $C_9H_9Cl_3N_2O_3S$; molecular weight = 331.60; Calculated: %C, 32.60; %H, 2.74; ;1 %Cl, 32.08; %N, 8.45; %S, 9.67; %C, 32.9; %H, 2.8; %Cl, 32.2; %N, 8.6; %S, 9.5.

EXAMPLE 22

N-METHYL-N-METHYLSULFONYL-N'-(3-TRIFLUOROMETHYLPHENYL)-UREA

A SOLUTION OF 11.4 g of N-methyl-N-methylsulfonyl-carbamoyl chloride in 100 ml of tetrahydrofuran was slowly added at 10° C to a mixture of 60 ml of tetrahydrofuran, 10.1 g of triethylamine and 16.1 g of 3-trifluoromethylaniline, and after stirring for 16 hours, the mixture was filtered. The filtrate was distilled to dryness under reduced pressure. The residue was added to isopropyl ether and the precipitate formed was recovered by vacuum filtration and was washed and dried to obtain 8 g of N-methyl-N-methylsulfonyl-N'-(3-trifluoromethylphenyl)-urea melting at 72° C. The melting point was unchanged after crystallization from isopropyl ether.

Analysis: $C_{10}H_{11}F_3N_2O_3S$; molecular weight = 296.27; Calculated: %C, 40.54; %H, 3.75; %F, 19.24; %N, 9.45; %S, 10.82; Found: %C, 40.2; %H, 3.9; %F, 19.3; %N, 9.4; %S, 11.1.

EXAMPLE 23

N-METHYL-N-ETHYLTHIO-N'-n-BUTYL-N'-(3,4-DICHLOROPHENYL)-UREA

STEP A: N-methyl-N'-n-butyl-N'-(3,4-dichlorophenyl)-urea

A mixture of 100 g of N-n-butyl-3,4-dichloroaniline (described in West German Pat. No. 1,902,419), 250 ml of isopropyl ether, 10 ml of triethylamine and 60 g of methyl isocyanate was stirred for 18 hours at room temperature and the solvent was distilled off under reduced pressure. The residue was added to petroleum ether (b.p.=65°-75° C) and after cooling, the precipitate formed was recovered by vacuum filtration to obtain 59 g of N-methyl-N'-n-butyl-N'-(3,4-dichlorophenyl)-urea melting at 58° C.

Analysis: $C_{12}H_{16}Cl_2N_2O$; molecular weight = 275.18; Calculated: %C, 52.38; %H, 5.86; %Cl, 25.77; %N, 10.18; Found: %C, 52.1; %H, 5.8; %Cl, 25.6; %N, 10.0.

STEP B: N-methyl-N-ethylthio-N'-n-butyl-N'-(3,4-dichlorophenyl)-urea

A mixture of 22.5 g of sulfuryl chloride and 30 ml of methylene chloride was slowly added at −40° C at 20.5 g of diethyldisulfide and 150 ml of methylene chloride and after raising the temperature to −5° C, the mixture was stirred for 5 minutes at that temperature to obtain a solution of ethane sulfenyl chloride. A solution of 45 g of N-methyl-N'-n-butyl-N'-(3,4-dichlorophenyl)-urea in 400 ml of pyridine was added to the said solution at −40° C and mixture was stirred for 2 hours at −40° C and then for 15 hours at 0° C and water was added. The mixture was stirred and decanted and the equeous phase was extracted with methylene chloride. The extract was washed, dried and concentrated to dryness under reduced pressure. the residue was chromatographed over silica gel and eluted with a 9-1 benzene-ethyl acetate mixture to obtain 22 g of N-methyl-N-ethylthio-N'-n-butyl-N'-(3,4-dichlorophenyl)-urea with a refractive index $n_D^{20}$ = 1.5585.

analysis: $C_{14}H_{20}Cl_2N_2OS$; molecular weight = 335.27; Calculated: %C, 50.15; %H, 6.02; %N, 8.36; %Cl, 21.15; %S, 9.56; Found: %C, 50.3; %H, 6.2; %N, 8.2; %Cl, 21.2; %S, 9.6.

EXAMPLE 24

N-METHYL-N,N'-DI-(4-MORPHOLINOTHIO)-N'-(3-TRIFLUOROMETHYLPHENYL)-UREA 3 g of a suspension of 50% sodium hydride in vaseline oil was added in small fractions to a solution of 20 g of N-methyl-N-thiomorpholino-N'-(3-trifluoromethylphenyl)-urea in 200 ml of tetrahydrofuran and the mixture was stirred at 20° C for 1 hour. A solution of 13.5 g of thiomorpholine chloride in 100 ml of tetrahydrofuran was added thereto at 10° C and after stirring for 4 hours at 20° C, the mixture was extracted with ethyl acetate. The organic phase was washed with water and dried and the residue was chromatographed over silica gel to obtain 10 g of N-methyl-N,N'-di-(4-morpholinothio)-N'-(3-trifluoromethylphenyl)-urea melting at 104° C.

Analysis: $C_{17}H_{23}H_{23}N_4F_3O_3S_2$; molecular weight = 452.52; Calculated: %C, 45.12; %H, 5.13; %N, 12.38; %F, 12.60; %S, 14.17; Found: %C, 45.4; %H, 5.2; %N, 12.4; %F, 12.7; %S, 13.9.

HERBICIDAL ACTIVITY

The test plants were grown in a culture flat (23 × 14 × 4 cm) having a double bottom and means for watering from below. The species were placed into a single flat at a ratio of 20 seeds per species, in rows spaced 3 cm apart. There were four sets of flats for each compound and concentration. The growing conditions were: temperature 20° C ± 2° C, humidity about 60%, lighting by a fluorescent tube (day light + brilliant white) from 6 hours to 22 hours each day. The soil mixture was composed of 10 volumes of earth, 10 volumes of river sand and 2 volumes of peat.

For the pre-emergence tests, the herbicidal treatment was carried out 24 hours after the seeds had been planted and the first watering was effected by sprinkling to carry the product to the seed level. the post-emergence tests were effected by 21 days after the plants appeared above ground. The test products were each applied under standard conditions with the aid of a microsprayer at doses of 5, 2.5, 1.25 and 0.625 kg/ha and at a dilution of 560 l/ha. Control tests without treatment were carried out in the same way. The final controls were effected by weight of the plants 21 days after treatment in the pre-emergence test and 15 days after treatment in the post-emergence test. The results were expressed as a percentage of mortality M $$M = \frac{\text{No. of control plants} - \text{No. of still living treated plants}}{\text{No. of control plants}} \times 100$$

except those results with an asterisk which are a percentage of reduction of weight of the vegetation P $$P = \frac{\text{weight of control plants} - \text{weight of treated plants}}{\text{weight of control plants}} \times 100$$

TABLE 1

Pre-emergence N-methyl-N-methylthio-N'-(3,4-dichlorophenyl)-urea.

|  | 5 Kg/ha | 2.5 Kg/ha | 1.25 Kg/ha | 0.625 Kg/ha |
|---|---|---|---|---|
| Bent grass | 76% | 62% | 76% | 42% |
| Oats | 61%* | 58%* | 39%* | 0% |
| Wheat | 38%* | 34%* | 22%* | 0% |
| Corn | 0% | 0% | 0% | 0% |
| Barley | 38% | 26% | 16%* | 15%* |
| Rye-grass | 100% | 100% | 100% | 53%* |
| Foxtail | 69% | 71% | 64% | 70% |
| Beets | 100% | 100% | 100% | 100% |
| Lambsquarter | 100% | 100% | 98% | 100% |
| Chrysanthemum | 100% | 100% | 97% | 97% |
| Mustard | 100% | 100% | 100% | 100% |
| Rumex | 100% | 100% | 100% | 100% |
| Clover | 100% | 100% | 75% | 89% |

TABLE 2

Pre-emergence N-methyl-N-2-thiapropyl-N'-(3,4-dichlorophenyl) urea.

|  | 5 Kg/ha | 2.5 Kg/ha | 1.25 Kg/ha | 0.625 Kg/ha |
|---|---|---|---|---|
| Oats | 47% | 0% | 0% | 0% |
| Wheat | 38%* | 32%* | 0% | 0% |
| Corn | 48%* | 33%* | 0% | 0% |
| Foxtail | 82% | 60% | 0% | 0% |
| Beets | 100% | 100% | 31% | 0% |
| Lambsquarter | 100% | 100% | 68% | 55% |
| Flax | 96% | 59%* | 0% | 0% |
| Mustard | 100% | 100% | 91% | 80% |
| Clover | 100% | 100% | 100% | 85% |

TABLE 3

Post emergence N-methyl-N-2-thiapropyl-N'-(3,4-dichlorophenyl)-urea.

|  | 5 Kg/ha | 2.5 Kg/ha | 1.25 Kg/ha | 0.625 Kg/ha |
|---|---|---|---|---|
| Oats | 68% | 51%* | 0% | 0% |
| Wheat | 67% | 39%* | 0% | 0% |
| Corn | 30% | 20% | 20% | 0% |
| Foxtail | 75% | 56% | 19%* | 0% |
| Beets | 100% | 100% | 100% | 100% |
| Lambsquarter | 100% | 100% | 100% | 100% |
| Flax | 100% | 100% | 100% | 0% |
| Mustard | 100% | 100% | 100% | 87% |
| Clover | 100% | 100% | 100% | 41% |

TABLE 4

Pre-emergence N-methyl-N-methylsulfonylmethyl-N'-(3,4-dichlorophenyl)-urea.

|  | 5 Kg/ha | 2.5 Kg/ha | 1.25 Kg/ha | 0.625 Kg/ha |
|---|---|---|---|---|
| Oats | 90% | 59%* | 0% | 0% |
| Wheat | 41% | 0% | 0% | 0% |
| Corn | 17%* | 0% | 0% | 0% |
| Foxtail | 95% | 72% | 20% | 19% |
| Beets | 100% | 100% | 100% | 80% |
| Lambsquarter | 100% | 100% | 100% | 100% |
| Flax | 86% | 65% | 41% | 0% |
| Mustard | 100% | 100% | 100% | 100% |
| Clover | 100% | 100% | 100% | 100% |

TABLE 5

Post emergence N-methyl-N-methylsulfonylmethyl-N'-(3,4-dichlorophenyl)-urea.

|  | 5 Kg/ha | 2.5 Kg/ha | 1.25 Kg/ha | 0.625 Kg/ha |
|---|---|---|---|---|
| Oats | 53%* | 44%* | 0% | 0% |
| Wheat | 6%* | 0% | 0% | 0% |
| Corn | 0% | 0% | 0% | 0% |
| Foxtail | 78% | 65% | 28%* | 0% |
| Beets | 100% | 100% | 100% | 93% |
| Lambsquarter | 100% | 100% | 100% | 100% |
| Flax | 100% | 100% | 48% | 0% |
| Mustard | 100% | 100% | 100% | 95% |
| Clover | 100% | 100% | 60% | 25% |

TABLE 6

Pre-emergence N-methyl-N-morpholinothio-N'-(3,4-dichlorophenyl)-urea.

|  | 5 Kg/ha | 2.5 Kg/ha | 1.25 Kg/ha | 0.625 Kg/ha |
|---|---|---|---|---|
| Oats | 56%* | 60%* | 0% | 0% |
| Wheat | 0% | 0% | 0% | 0% |
| Corn | 0% | 0% | 0% | 0% |
| Foxtail | 70%* | 69%* | 52%* | 50%* |
| Beets | 100% | 100% | 95% | 91% |
| Lambsquarter | 100% | 100% | 100% | 100% |
| Flax | 89% | 30% | 30% | 16% |
| Mustard | 100% | 100% | 100% | 100% |
| Clover | 100% | 100% | 100% | 100% |

TABLE 7

Post emergence N-methyl-N-morpholinothio-N'-(3,4-dichlorophenyl)-urea.

|  | 5 Kg/ha | 2.5 Kg/ha | 1.25 Kg/ha | 0.625 Kg/ha |
|---|---|---|---|---|
| Oats | 21% | 0% | 0% | 0% |
| Wheat | 0% | 0% | 0% | 0% |
| Corn | 0% | 0% | 0% | 0% |
| Foxtail | 74%* | 71%* | 58%* | 0% |
| Beets | 100% | 100% | 100% | 100% |
| Lambsquarter | 100% | 100% | 100% | 100% |
| Flax | 100% | 100% | 21% | 0% |
| Mustard | 100% | 100% | 100% | 100% |
| Clover | 100% | 100% | 65% | 60% |

TABLE 8

Pre-emergence N-methyl-N-ethylthio-N'-(3-chloro-4-methoxyphenyl)-urea.

|  | 5 Kg/ha | 2.5 Kg/ha | 1.25 Kg/ha | 0.625 Kg/ha |
|---|---|---|---|---|
| Bent grass | 100% | 100% | 100% | 100% |
| Oats | 70% | 67%* | 50%* | 43%* |
| Wheat | 32%* | 0% | 0% | 0% |
| Corn | 0% | 0% | 0% | 0% |
| Barley | 50%* | 41%* | 28%* | 0% |
| Rye-grass | 100% | 66% | 53% | 34% |
| Foxtail | 63%* | 78%* | 57%* | 70%* |
| Beets | 100% | 100% | 100% | 79% |
| Lambsquarter | 100% | 100% | 100% | 100% |
| Chrysanthemum | 100% | 100% | 100% | 100% |
| Gaillet | 55% | 27% | 0% | 0% |
| Mustard | 100% | 100% | 100% | 100% |
| Rumex | 100% | 100% | 100% | 100% |
| Clover | 100% | 100% | 100% | 79% |

TABLE 9

Post-emergence N-methyl-N-ethylthio-N'-(3-chloro-4-methoxyphenyl)-urea.

|  | 5 Kg/ha | 2.5 Kg/ha | 1.25 Kg/ha | 0.625 Kg/ha |
|---|---|---|---|---|
| Bent grass | 100% | 100% | 100% | 82% |
| Oats | 100% | 87% | 73%* | 51%* |
| Wheat | 100% | 53% | 28% | 0% |
| Corn | 55% | 56%* | 34%* | 42%* |
| Barley | 100% | 58% | 38% | 0% |
| Rye-grass | 100% | 100% | 73%* | 38%* |
| Foxtail | 100% | 50% | 67%* | 64%* |
| Beets | 100% | 100% | 100% | 100% |
| Lambsquarter | 100% | 100% | 100% | 100% |
| Chrysanthemum | 100% | 100% | 100% | 97% |
| Gaillet | 69% | 69% | 41% | 54% |
| Mustard | 100% | 100% | 100% | 85% |
| Rumex | 100% | 100% | 100% | 82% |
| Clover | 100% | 68% | 63%* | 71%* |

TABLE 10

Pre-emergence N-methyl-N-ethylthio-N'-(3-chloro-4-methylphenyl)-urea.

|  | 5 Kg/ha | 2.5 Kg/ha | 1.25 Kg/ha | 0.625 Kg/ha |
|---|---|---|---|---|
| Bent grass | 100% | 100% | 90% | 100% |
| Oats | 100% | 100% | 64%* | 73%* |
| Wheat | 42% | 36% | 0% | 0% |
| Corn | 0% | 0% | 0% | 0% |
| Barley | 100% | 100% | 0% | 0% |
| Rye-grass | 100% | 100% | 100% | 100% |
| Foxtail | 100% | 100% | 100% | 42% |
| Beets | 100% | 100% | 100% | 100% |
| Lambsquarter | 100% | 100% | 100% | 100% |
| Chrysanthemum | 100% | 100% | 100% | 100% |
| Gaillet | 65%* | 73%* | 67%* | 45%* |
| Mustard | 100% | 100% | 100% | 100% |
| Rumex | 100% | 100% | 100% | 100% |
| Clover | 100% | 100% | 100% | 100% |

TABLE 11

Post-emergence N-methyl-N-ethylthio-N'-(3-chloro-4-methylphenyl)-urea.

|  | 5 Kg/ha | 2.5 Kg/ha | 1.25 Kg/ha | 0.625 Kg/ha |
|---|---|---|---|---|
| Bent grass | 100% | 100% | 65% | 62% |
| Oats | 90% | 46% | 52%* | 34%* |
| Wheat | 85% | 0% | 0% | 0% |
| Corn | 57% | 42% | 0% | 0% |
| Barley | 63% | 0% | 0% | 0% |
| Rye-grass | 100% | 100% | 54%* | 40%* |
| Foxtail | 100% | 80% | 36% | 0% |
| Beets | 100% | 100% | 100% | 100% |
| Lambsquarter | 100% | 100% | 100% | 100% |
| Chrysanthemum | 100% | 100% | 100% | 100% |
| Gaillet | 100% | 100% | 100% | 51% |
| Mustard | 100% | 100% | 100% | 67% |
| Rumex | 100% | 100% | 100% | 59% |
| Clover | 100% | 100% | 100% | 61% |

TABLE 12

Pre-emergence N-methyl-N-ethylthio-N'-(3-trifluoromethylphenyl)-urea.

|  | 5 Kg/ha | 2.5 Kg/ha | 1.25 Kg/ha | 0.625 Kg/ha |
|---|---|---|---|---|
| Bent grass | 100% | 100% | 100% | 100% |
| Oats | 77%* | 64%* | 46%* | 31%* |
| Wheat | 55%* | 46%* | 39%* | 38%* |
| Corn | 0% | 0% | 0% | 0% |
| Barley | 51%* | 31%* | 0% | 0% |
| Rye-grass | 100% | 100% | 43% | 56%* |
| Foxtail | 100% | 40% | 67%* | 61%* |
| Beets | 100% | 100% | 100% | 100% |
| Lambsquarter | 100% | 100% | 100% | 100% |
| Chrysanthemum | 100% | 100% | 100% | 100% |
| Gaillet | 39%* | 30%* | 34%* | 34%* |
| Mustard | 100% | 100% | 100% | 100% |
| Rumex | 100% | 100% | 100% | 100% |
| Clover | 100% | 100% | 100% | 100% |

TABLE 13

Post-emergence N-methylN-ethylthio-N'-(3-trifluoromethylphenyl)-urea

|  | 5 Kg/ha | 2.5 Kg/ha | 1.25 Kg/ha | 0.625 Kg/ha |
|---|---|---|---|---|
| Bent grass | 100% | 100% | 79% | 47% |
| Oats | 44% | 60%* | 35%* | 0% |
| Wheat | 42% | 0% | 0% | 0% |
| Corn | 90% | 52%* | 28%* | 0% |
| Barley | 43% | 36% | 0% | 0% |
| Rye-grass | 93% | 66% | 53%* | 37%* |
| Foxtail | 76% | 46% | 0% | 0% |
| Beets | 100% | 100% | 100% | 100% |
| Lambsquarter | 100% | 100% | 100% | 100% |
| Chrysanthemum | 100% | 100% | 93% | 70% |
| Gaillet | 100% | 100% | 44% | 23% |
| Mustard | 100% | 100% | 30% | 40% |
| Rumex | 100% | 100% | 33% | 40% |
| Clover | 100% | 100% | 56% | 25% |

TABLE 14

Pre-emergence N-methyl-N-ethylthio-N'-(4-bromophenyl)-urea.

|  | 5 Kg/ha | 2.5 Kg/ha | 1.25 Kg/ha | 0.625 Kg/ha |
|---|---|---|---|---|
| Bent grass | 100% | 100% | 100% | 46%* |
| Oats | 50% | 39% | 0% | 0% |
| Wheat | 0% | 0% | 0% | 0% |
| Corn | 0% | 0% | 0% | 0% |
| Barley | 29% | 0% | 0% | 0% |
| Rye-grass | 100% | 45% | 58% | 50% |
| Foxtail | 73%* | 40%* | 35%* | 0% |
| Beets | 100% | 100% | 29% | 0% |
| Lambsquarter | 100% | 100% | 100% | 48% |
| Chrysanthemum | 100% | 100% | 100% | 100% |
| Gaillet | 44% | 27% | 0% | 0% |
| Mustard | 100% | 100% | 100% | 68% |
| Rumex | 100% | 100% | 100% | 47% |
| Clover | 100% | 100% | 100% | 100% |

TABLE 15

Post-emergence N-methyl-N-ethylthio-N'-(4-bromophenyl)-urea.

|  | 5 Kg/ha | 2.5 Kg/ha | 1.25 Kg/ha | 0.625 Kg/ha |
|---|---|---|---|---|
| Bent grass | 100% | 100% | 100% | 100% |
| Oats | 100% | 100% | 29% | 44% |
| Wheat | 100% | 100% | 38% | 0% |
| Corn | 30% | 55% | 34% | 0% |
| Barley | 100% | 100% | 52%* | 0% |
| Rye-grass | 100% | 100% | 59% | 32% |
| Foxtail | 100% | 100% | 60% | 62%* |
| Beets | 100% | 100% | 100% | 100% |
| Lambsquarter | 100% | 100% | 100% | 100% |
| Chrysanthemum | 100% | 100% | 100% | 100% |
| Gaillet | 100% | 100% | 100% | 50% |
| Mustard | 100% | 100% | 100% | 100% |
| Rumex | 100% | 100% | 100% | 100% |
| Clover | 100% | 100% | 100% | 100% |

TABLE 16

Pre-emergence N-methyl-N-(4-morpholinothio)-N'-(3-trifluormethylphenyl)-urea.

|  | 5 Kg/ha | 2.5 Kg/ha | 1.25 Kg/ha | 0.625 Kg/ha |
|---|---|---|---|---|
| Bent grass | 100% | 100% | 76%* | 55%* |
| Oats | 71%* | 46%* | 0% | 0% |
| Wheat | 22% | 0% | 0% | 0% |
| Corn | 0% | 0% | 0% | 0% |
| Barley | 39%* | 32%* | 0% | 0% |
| Rye-grass | 100% | 80% | 0% | 0% |
| Foxtail | 59%* | 53%* | 0% | 0% |
| Beets | 100% | 71%* | 58%* | 67%* |
| Lambsquarter | 100% | 100% | 55%* | 60%* |
| Chrysanthemum | 100% | 100% | 80%* | 55%* |
| Gaillet | 0% | 0% | 0% | 0% |
| Mustard | 100% | 100% | 94%* | 96%* |
| Rumex | 100% | 91%* | 61%* | 53%* |
| Clover | 100% | 100% | 100% | 100% |

TABLE 17

Pre-emergence N-methyl-N-propylthio-N'-(3,4-dichlorophenyl urea.

|  | 5 Kg/ha | 2.5 Kg/ha | 1.25 Kg/ha | 0.625 Kg/ha |
|---|---|---|---|---|
| Bent grass | 100% | 100% | 92% | 77% |
| Oats | 100% | 83%* | 47%* | 0% |
| Wheat | 54%* | 29%* | 0% | 0% |
| Corn | 20%* | 0% | 0% | 0% |
| Barley | 69%* | 32%* | 0% | 0% |
| Rye-grass | 100% | 95% | 76%* | 0% |
| Foxtail | 89%* | 79%* | 68%* | 0% |
| Beets | 100% | 100% | 89% | 67% |
| Lambsquarter | 100% | 100% | 87% | 53% |
| Chrysanthemum | 100% | 100% | 100% | 95% |
| Mustard | 100% | 100% | 100% | 97%* |
| Rumex | 100% | 100% | 68%* | 38%* |
| Clover | 100% | 100% | 97%* | 99%* |

TABLE 18

Pre-emergence N-methyl-N-n-butylthio-N'-(3,4,-dichlorophenyl)-urea.

|  | 5 Kg/ha | 2.5 Kg/ha | 1.25 Kg/ha | 0.625 Kg/ha |
|---|---|---|---|---|
| Bent grass | 100% | 89% | 93%* | 83%* |
| Oats | 100% | 61%* | 0% | 0% |
| Wheat | 46%* | 0% | 0% | 0% |
| Corn | 0% | 0% | 0% | 0% |
| Barley | 71%* | 0% | 0% | 0% |
| Rye-grass | 100% | 97%* | 80%* | 0% |
| Foxtail | 86%* | 56%* | 48%* | 0% |
| Beets | 100% | 99% | 86% | 83% |
| Lambsquarter | 100% | 100% | 96% | 83% |
| Chrysanthemum | 100% | 100% | 100% | 100% |
| Mustard | 100% | 100% | 100% | 100% |
| Rumex | 100% | 100% | 100% | 100% |
| Clover | 100% | 100% | 100% | 100% |

The results of the above tables clearly show that the compounds of formula I have good pre- and post-emergence herbicidal activity against dicotyledons and are slightly active against grasses, particularly cultivated grasses which make them useful as selective herbicides for cereal crops.

The following tests were conducted to compare the pre- and post-emergence herbicidal activity to the compounds of the above application and Linuron /3-(3,4-dichlorophenyl)-1-methoxy-1-methyl-urea/. The test plants were grown in a culture flat (23 × 14 × 4 cm) having a double bottom and means for watering from below. The species were placed into a single flat at a ratio of 20 seeds per species, in rows spaced 3 cm apart. There were four sets of flats for each compound and concentration. The growing conditions were: temperature 20° C ± 2° C, humidity 60%, lighting by a fluorescent tube (day light + brilliant white) from 6 hours to 22 hours each day. The soil mixture was composed of 10 volumes of earth, 10 volumes of river sand and 2 volumes of peat.

For the pre-emergence tests, the herbicidal treatment was carried out 24 hours after the seeds had been planted and the first watering was effected by sprinkling to carry the product to the seed level. The post-emergence tests were effected by 21 days after the plants appeared above ground. The test products were each applied under standard conditions with the aid of a microsprayer at doses of 5, 2.5, 1.25 and 0.625 kg/ha and at a dilution of 560 l/ha. Control tests without treatment were carried out in the same way. The final controls were effected by weight of the plants 21 days after treatment in the pre-emergence test and 15 days after treatment in the post-emergence test. The results were expressed as a percentage of mortality of the plants calculated as the ratio of plants killed to the plants treated. The results are reported in Table 19.

TABLE 19

| Treatment | Test Product | Plant treated | Dose in Kg/ha | % Mortality | Reduction in weight |
|---|---|---|---|---|---|
| Post Emergence | N-methyl-N-isopropylthio-N'-(3,4-dichlorophenyl)-urea-Ex 18 | Carrots | 1.25 | 100 | — |
| | | | 0.6 | 58 | 83 |
| | Linuron | Carrots | 1.5 | 15 | 24 |
| | | | 0.75 | 10 | 10 |
| Post Emergence | N-methyl-N-ethylthio-N'-(3,4-dichlorophenyl)-urea -Ex 6 | Carrots | 1.25 | 100 | — |
| | | | 0.6 | 33 | 28 |
| | Linuron | Carrots | 1.5 | 0 | 0 |
| | | | 0.75 | 0 | 0 |
| Post Emergence | N-methyl-N-ethylthio-N'-(3,4-dichlorophenyl)-urea -Ex 6 | Bermuda grass | 0.6 | 70 | 81 |
| | | Panic grass | 0.6 | 65 | 69 |
| | Linuron | Bermuda grass | 0.62 | 10 | 49 |
| | | Panic grass | 0.62 | 17 | 37 |
| Pre Emergence | N-methyl-N-ethylthio-N'-(3,4-dichlorophenyl)-urea -Ex 6 | Carrots | 1.25 | 100 | — |
| | | | 0.6 | 93 | 94 |
| | Linuron | Carrots | 1.5 | 0 | 0 |
| | | | 0.6 | 0 | 0 |

The data of the above Table clearly shows the herbicidal superiority of the products of the above application as compared to Linuron in these tests. For example, the product of Example 6 of the application has a post-emergence herbicidal activity against carrots, bermuda grass and panic grass which is 3 to 6 greater than Linuron and when applied pre-emergence to carrots at 1.25 and 0.6 Kg/ha, the product of Example 6 is substantially totally effective while Linuron has no activity at these doses. The product of Example 18 of the above application in a post-emergence test against carrots shows an activity about 6 times greater than Linuron.

Using the pre- and post-emergence herbicidal tests described above, the products of Examples 6 and 18 were compared to the corresponding N-ethoxy derivatives of U.S. Pat. No. 3,288,586 and the results are reported in Tables 20 to 23.

TABLE 20

N-methyl-N-ethylthio-N'-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 65 | 58 | 50 | 44 | 100 | 100 | 85 | 51 |
| Wheat | 0 | 0 | 0 | 0 | 100 | 69 | 47 | 0 |
| Barley | 51 | 32 | 0 | 0 | 100 | 74 | 50 | 0 |
| Corn | 0 | 0 | 0 | 0 | 66 | 52 | 0 | 0 |
| Bent grass | 100 | 100 | 95 | 82 | 100 | 100 | 100 | 62 |
| Rye grass | 100 | 100 | 100 | 100 | 100 | 100 | 100 | 100 |
| Foxtail | 75 | 76 | 72 | 58 | 100 | 100 | 100 | 61 |
| Beets | 100 | 100 | 100 | 100 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 100 | 100 |
| Gaillet | — | — | — | — | — | — | — | — |
| Mustard | 100 | 100 | 100 | 100 | 100 | 100 | 100 | 100 |
| Rumex | 100 | 100 | 100 | 100 | 100 | 100 | 100 | 100 |

TABLE 20-continued

N-methyl-N-ethylthio-N'-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Clover | 100 | 100 | 100 | 100 | 100 | 100 | 100 | 100 |

TABLE 21

N-methyl-N-ethoxy-N'-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 0 | 0 | 0 | 0 | 100 | 66 | 0 | 0 |
| Wheat | 0 | 0 | 0 | 0 | 14 | 0 | 0 | 0 |
| Barley | 0 | 0 | 0 | 0 | 55 | 29 | 0 | 0 |
| Corn | 0 | 0 | 0 | 0 | 32 | 21 | 0 | 0 |
| Bent grass | 0 | 0 | 0 | 0 | 100 | 100 | 33 | 0 |
| Rye grass | 82 | 0 | 0 | 0 | 100 | 100 | 32 | 0 |
| Foxtail | 0 | 0 | 0 | 0 | 75 | 0 | 0 | 0 |
| Beets | 100 | 100 | 100 | 72 | 100 | 100 | 100 | 100 |
| Lambsquarter | 100 | 100 | 100 | 66 | 100 | 100 | 100 | 100 |
| Chrysanthemum | 100 | 100 | 100 | 91 | 100 | 100 | 100 | 100 |
| Gaillet | 23 | 0 | 0 | 0 | 100 | 100 | 86 | 36 |
| Mustard | 100 | 100 | 100 | 67 | 100 | 100 | 100 | 100 |
| Rumex | 100 | 100 | 100 | 68 | 100 | 100 | 100 | 100 |
| Clover | 100 | 100 | 100 | 73 | 100 | 100 | 100 | 100 |

TABLE 22

N-methyl-N-isopropylthio-N-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 100 | 54 | 0 | 0 | 100 | 100 | 81 | 0 |
| Wheat | 0 | 0 | 0 | 0 | 100 | 40 | 58 | 0 |
| Barley | 40 | 0 | 0 | 0 | 100 | 88 | 100 | 0 |
| Corn | 0 | 0 | 0 | 0 | 80 | 45 | 35 | 0 |
| Bent grass | 100 | 100 | 55 | 0 | 100 | 100 | 100 | 86 |
| Rye grass | 100 | 100 | 100 | 90 | 100 | 100 | 100 | 35 |
| Foxtail | 0 | 0 | 0 | 0 | 100 | 100 | 54 | 0 |
| Beets | 100 | 100 | 100 | 100 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 100 | 100 |
| Gaillet | 48 | 0 | 0 | 0 | 100 | 100 | 100 | 100 |
| Mustard | 100 | 100 | 100 | 100 | 100 | 100 | 100 | 100 |
| Rumex | 100 | 100 | 100 | 100 | 100 | 100 | 100 | 100 |
| Clover | 100 | 100 | 100 | 100 | 100 | 100 | 100 | 100 |

TABLE 23

N-methyl-N-isopropoxy-N'-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |

TABLE 23-continued

N-methyl-N-isopropoxy-N'-(3',4'-dichlorophenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Corn | 0 | 0 | 0 | 0 | 0 | 0 | 0 | 0 |
| Bent grass | 0 | 0 | 0 | 0 | 0 | 0 | 0 | 0 |
| Rye grass | 0 | 0 | 0 | 0 | 0 | 0 | 0 | 0 |
| Foxtail | 0 | 0 | 0 | 0 | 0 | 0 | 0 | 0 |
| Beets | 100 | 100 | 43 | 43 | 100 | 100 | 100 | 62 |
| Lambsquarter | 100 | 100 | 76 | 60 | 100 | 100 | 100 | 100 |
| Chrysanthemum | 85 | 47 | 0 | 0 | 29 | 0 | 0 | 0 |
| Gaillet | 40 | 0 | 0 | 0 | 100 | 90 | 26 | 0 |
| Mustard | 100 | 100 | 94 | 69 | 100 | 100 | 100 | 100 |
| Rumex | 100 | 100 | 60 | 32 | 100 | 100 | 100 | 92 |
| Clover | 66 | 73 | 63 | 27 | 39 | 28 | 32 | 33 |

The data in Tables 20 to 23 clearly show that the compounds of the invention possess an unexpectedly superior herbicidal activity as compared to their corresponding oxygen analogs when applied either pre- or post-emergence.

Using the above procedure, the N-methyl-N-alkylthio compounds of the invention were compared with the corresponding oxygen analogs of U.S. Pat. Nos. 3,165,549 and 3,228,762 and the said test data clearly shows the superior herbicidal activity of the claimed thio compounds.

TABLE 24

N-methyl-N-ethylthio-N'-(3'-trifluoromethylphenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 77* | 64* | 46* | 31* | 44 | 60* | 35* | 0 |
| Wheat | 55* | 46* | 39* | 38* | 42 | 0 | 0 | 0 |
| Barley | 51* | 31* | 0 | 0 | 43 | 36 | 0 | 0 |
| Corn | 0 | 0 | 0 | 0 | 90 | 52* | 28* | 0 |
| Bent grass | 100 | 100 | 100 | 100 | 100 | 100 | 79 | 47 |
| Rye grass | 100 | 100 | 43 | 56 | 93 | 66 | 53* | 37* |
| Foxtail | 100 | 40 | 67* | 61* | 76 | 46 | 0 | 0 |
| Beets | 100 | 100 | 100 | 100 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 93 | 70 |
| Gaillet | 39 | 30 | 34 | 34 | 100 | 100 | 44 | 23 |
| Mustard | 100 | 100 | 100 | 100 | 100 | 100 | 30 | 48 |
| Rumex | 100 | 100 | 100 | 100 | 100 | 100 | 33 | 40 |
| Clover | 100 | 100 | 100 | 100 | 100 | 100 | 56 | 25 |

TABLE 25

N-methyl-N-isopropylthio-N'-(3-trifluoromethylphenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 35 | 40 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 24 | 0 | 0 | 0 | 12 | 0 | 0 | 0 |
| Bent grass | 90 | 81 | 65 | 0 | 100 | 100 | 0 | 0 |
| Rye grass | 88 | 78 | 20 | 0 | 36 | 0 | 0 | 0 |
| Foxtail | 42 | 32 | 0 | 0 | 0 | 0 | 0 | 0 |
| Beets | 100 | 100 | 100 | 63 | 100 | 93 | 55 | 21 |
| Lambsquarter | 100 | 100 | 100 | 100 | 100 | 100 | 100 | 100 |
| Chrysanthemum | 100 | 100 | 100 | 100 | 100 | 64 | 37 | 0 |
| Gaillet | 81 | 28 | 0 | 0 | 77 | 60 | 0 | 0 |
| Mustard | 100 | 100 | 85 | 73 | 100 | 100 | 89 | 89 |
| Rumex | 100 | 100 | 79 | 62 | 100 | 100 | 83 | 37 |
| Clover | 100 | 100 | 100 | 63 | 100 | 75 | 0 | 0 |

TABLE 26

N-methyl-N-isopropoxy-N'-(3'-trifluoromethylphenyl)-urea

| | Pre-Emergence | | | | Post-Emergence | | | |
|---|---|---|---|---|---|---|---|---|
| Doses Kg/ha | 5 | 2.5 | 1.25 | 0.625 | 5 | 2.5 | 1.25 | 0.625 |
| Oats | 35 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 0 | 0 | 0 | 0 | 0 | 0 | 0 | 0 |
| Bent grass | 67 | 0 | 0 | 0 | 0 | 0 | 0 | 0 |
| Rye grass | 0 | 0 | 0 | 0 | 0 | 0 | 0 | 0 |
| Foxtail | 0 | 0 | 0 | 0 | 0 | 0 | 0 | 0 |
| Beets | 49 | 0 | 0 | 0 | 0 | 0 | 0 | 0 |
| Lambsquarter | 100 | 83 | 0 | 0 | 100 | 57 | 0 | 0 |
| Chrysanthemum | 68 | 54 | 32 | 0 | 0 | 0 | 0 | 0 |
| Gaillet | 0 | 0 | 0 | 0 | 0 | 0 | 0 | 0 |
| Mustard | 95 | 93 | 30 | 0 | 0 | 0 | 0 | 0 |
| Rumex | 56 | 32 | 0 | 0 | 0 | 0 | 0 | 0 |
| Clover | 0 | 0 | 0 | 0 | 0 | 0 | 0 | 0 |

TABLE 27

N-Methyl-N-ethylthio-N'-(4-methyl-3-chlorophenyl)-urea

| | re-Emergence | | | | Post-Emergence | | | |
|---|---|---|---|---|---|---|---|---|
| Dose Kg/ha | 5 | 2.5 | 1.25 | 0.625 | 5 | 2.5 | 1.25 | 0.625 |
| Oats | 42 | 36 | 0 | 0 | 85 | 0 | 0 | 0 |
| Wheat | 100 | 100 | 0 | 0 | 63 | 0 | 0 | 0 |
| Barley | 0 | 0 | 0 | 0 | 57 | 42 | 0 | 0 |
| Corn | 100 | 100 | 64* | 73* | 90 | 46 | 52* | 34* |
| Bent grass | 100 | 100 | 90 | 100 | 100 | 100 | 65 | 62 |
| Rye grass | 100 | 100 | 100 | 100 | 100 | 100 | 54* | 40* |
| Foxtail | 100 | 100 | 100 | 42 | 100 | 80 | 36 | 0 |
| Beets | 100 | 100 | 100 | 100 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 100 | 100 |
| Gaillet | 65* | 73* | 67* | 45* | 100 | 100 | 100 | 51 |
| Mustard | 100 | 100 | 100 | 100 | 100 | 100 | 100 | 67 |
| Rumex | 100 | 100 | 100 | 100 | 100 | 100 | 100 | 59 |

TABLE 27-continued

| | N-Methyl-N-ethylthio-N'-(4-methyl-3-chlorophenyl)-urea | | | | | | | |
|---|---|---|---|---|---|---|---|---|
| | re-Emergence | | | | Post-Emergence | | | |
| Dose Kg/ha | 5 | 2.5 | 1.25 | 0.625 | 5 | 2.5 | 1.25 | 0.625 |
| Clover | 100 | 100 | 100 | 100 | 100 | 100 | 100 | 64 |

TABLE 28

| | N-methyl-N-isopropylthio-N'-(3-chloro-4-methylphenyl)-urea | | | | | | | |
|---|---|---|---|---|---|---|---|---|
| | Pre-Emergence | | | | Post-Emergence | | | |
| Doses Kg/ha | 5 | 2.5 | 1.25 | 0.625 | 5 | 2.5 | 1.25 | 0.625 |
| Oats | 0 | 0 | 0 | 0 | 100 | 100 | 83 | 34 |
| Wheat | 32 | 0 | 0 | 0 | 0 | 0 | 0 | 0 |
| Barley | 100 | 0 | 0 | 0 | 100 | 62 | 50 | 20 |
| Corn | 0 | 0 | 0 | 0 | 65 | 30 | 100 | 0 |
| Bent grass | 100 | 93 | 0 | 0 | 100 | 100 | 100 | 84 |
| Rye grass | 100 | 96 | 90 | 16 | 100 | 100 | 100 | 0 |
| Foxtail | 100 | 100 | 43 | 0 | 100 | 100 | 42 | 0 |
| Beets | 100 | 100 | 67 | 19 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 100 | 100 |
| Gaillet | 43 | 0 | 0 | 0 | — | — | — | — |
| Mustard | 100 | 100 | 100 | 100 | 100 | 100 | 100 | 100 |
| Rumex | 100 | 100 | 100 | 100 | 100 | 100 | 100 | 100 |
| Clover | 100 | 100 | 100 | 100 | 100 | 100 | 100 | 100 |

TABLE 29

| | N-methyl-N-ethoxy-N'-(3-chloro-4-methylphenyl)-urea | | | | | | | |
|---|---|---|---|---|---|---|---|---|
| | Pre-Emergence | | | | Post-Emergence | | | |
| Doses Kg/ha | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 20 | 0 | 0 | 0 | 0 | 0 | 0 | 0 |
| Bent grass | 0 | 0 | 0 | 0 | 83 | 0 | 0 | 0 |
| Rye grass | 37 | 58 | 38 | 0 | 0 | 0 | 0 | 0 |
| Foxtail | 0 | 0 | 0 | 0 | 0 | 0 | 0 | 0 |
| Beets | 100 | 74 | 74 | 0 | 100 | 100 | 100 | 39 |
| Lambsquarter | 100 | 100 | 100 | 42 | 100 | 100 | 100 | 100 |
| Chrysanthemum | 100 | 100 | 71 | 66 | 100 | 100 | 86 | 55 |
| Gaillet | 0 | 0 | 0 | 0 | 39 | 0 | 0 | 0 |
| Mustard | 100 | 100 | 63 | 40 | 100 | 100 | 65 | 42 |
| Rumex | 100 | 100 | 68 | 50 | 100 | 100 | 100 | 77 |
| Clover | 100 | 100 | 68 | 55 | 100 | 100 | 94 | 45 |

TABLE 30

| | N-methyl-N-isopropoxy-N'-(3-chloro-4-methylphenyl)-urea | | | | | | | |
|---|---|---|---|---|---|---|---|---|
| | Pre-Emergence | | | | Post-Emergence | | | |
| Doses Kg/ha | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 0 | 0 | 0 | 0 | 0 | 0 | 0 | 0 |
| Bent grass | 0 | 0 | 0 | 0 | 0 | 0 | 0 | 0 |
| Rye grass | 0 | 0 | 0 | 0 | 0 | 0 | 0 | 0 |
| Foxtail | 0 | 0 | 0 | 0 | 0 | 0 | 0 | 0 |
| Beets | 29 | 0 | 0 | 0 | 100 | 25 | 0 | 0 |
| Lambsquarter | 67 | 0 | 0 | 0 | 100 | 90 | 58 | 69 |
| Chrysanthemum | 41 | 27 | 0 | 0 | 41 | 0 | 0 | 0 |
| Gaillet | 0 | 0 | 0 | 0 | 0 | 0 | 0 | 0 |
| Mustard | 85 | 70 | 38 | 0 | 100 | 68 | 0 | 0 |
| Rumex | 15 | 0 | 0 | 0 | 100 | 45 | 0 | 0 |
| Clover | 55 | 0 | 0 | 0 | 100 | 0 | 0 | 0 |

TABLE 31

| | N-methyl-N-butoxy-N'-(3-chloro-4-methylphenyl)-urea | | | | | | | |
|---|---|---|---|---|---|---|---|---|
| | Pre-Emergence | | | | Post-Emergence | | | |
| Doses Kg/ha | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 0 | 0 | 0 | 0 | 0 | 0 | 0 | 0 |
| Bent grass | 0 | 0 | 0 | 0 | 0 | 0 | 0 | 0 |
| Rye grass | 0 | 0 | 0 | 0 | 0 | 0 | 0 | 0 |
| Foxtail | 0 | 0 | 0 | 0 | 0 | 0 | 0 | 0 |
| Beets | 51 | 23 | 0 | 0 | 100 | 100 | 0 | 0 |
| Lambsquarter | 58 | 0 | 0 | 0 | 100 | 100 | 100 | 100 |
| Chrysanthemum | 68 | 54 | 32 | 0 | 0 | 0 | 0 | 0 |
| Gaillet | 0 | 0 | 0 | 0 | 100 | 38 | 0 | 0 |
| Mustard | 80 | 40 | 0 | 0 | 100 | 100 | 29 | 0 |
| Rumex | 62 | 0 | 0 | 0 | 100 | 100 | 0 | 0 |
| Clover | 68 | 29 | 0 | 0 | 0 | 0 | 0 | 0 |

TABLE 32

| | N-methyl-N-ethylthio-N'-(3-chloro-4-methoxyphenyl)-urea | | | | | | | |
|---|---|---|---|---|---|---|---|---|
| | Pre-Emergence | | | | Post-Emergence | | | |
| Doses Kg/ha | 5 | 2.5 | 1.25 | 0.625 | 5 | 2.5 | 1.25 | 0.625 |
| Oats | 70 | 67* | 50* | 43* | 100 | 87 | 73 | 51 |
| Wheat | 32 | 0 | 0 | 0 | 100 | 53 | 28 | 0 |
| Barley | 50* | 41* | 28* | 0 | 100 | 58 | 38 | 0 |
| Corn | 0 | 0 | 0 | 0 | 55 | 56* | 34* | 42* |
| Bent grass | 100 | 100 | 100 | 100 | 100 | 100 | 100 | 82 |
| Rye grass | 100 | 66 | 53 | 34 | 100 | 100 | 73 | 38 |
| Foxtail | 63* | 78* | 57* | 70* | 100 | 50 | 67* | 64* |
| Beets | 100 | 100 | 100 | 79 | 100 | 100 | 100 | 100 |
| Lambsquarter | 100 | 100 | 100 | 100 | 100 | 100 | 100 | 100 |
| Chrysanthemum | 100 | 100 | 100 | 100 | 100 | 100 | 100 | 97 |
| Gaillet | 55 | 27 | 0 | 0 | 69 | 69 | 41 | 54 |
| Mustard | 100 | 100 | 100 | 100 | 100 | 100 | 100 | 85 |

TABLE 32-continued

N-methyl-N-ethylthio-N'-(3-chloro-4-methoxyphenyl)-urea

| Doses Kg/ha | Pre-Emergence | | | | Post-Emergence | | | |
|---|---|---|---|---|---|---|---|---|
| | 5 | 2.5 | 1.25 | 0.625 | 5 | 2.5 | 1.25 | 0.625 |
| Rumex | 100 | 100 | 100 | 100 | 100 | 100 | 100 | 82 |
| Clover | 100 | 100 | 100 | 79 | 100 | 68 | 63* | 71* |

TABLE 33

N-methyl-N-isopropylthio-N-(3-chloro-4-methoxyphenyl)-urea

| Doses Kg/ha | Pre-Emergence | | | | Post-Emergence | | | |
|---|---|---|---|---|---|---|---|---|
| | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 0 | 0 | 0 | 0 | 0 | 0 | 0 | 0 |
| Bent grass | 100 | 85 | 0 | 0 | 95 | 79 | 0 | 0 |
| Rye grass | 33 | 0 | 0 | 0 | 0 | 0 | 0 | 0 |
| Foxtail | 0 | 0 | 0 | 0 | 0 | 0 | 0 | 0 |
| Beets | 100 | 77 | 37 | 0 | 100 | 100 | 100 | 82 |
| Lambsquarter | 100 | 100 | 100 | 83 | 100 | 100 | 100 | 100 |
| Chrysanthemum | 100 | 100 | 100 | 66 | 100 | 66 | 43 | 0 |
| Gaillet | 83 | 64 | 0 | 0 | 100 | 100 | 93 | 79 |
| Mustard | 100 | 100 | 55 | 28 | 100 | 100 | 100 | 100 |
| Rumex | 100 | 65 | 53 | 24 | 100 | 100 | 100 | 0 |
| Clover | 100 | 66 | 0 | 0 | 93 | 88 | 78 | 23 |

TABLE 34

N-methyl-N-isopropoxy-N'-(3-chloro-4-methoxyphenyl)-urea

| Doses Kg/ha | Pre-Emergence | | | | Post-Emergence | | | |
|---|---|---|---|---|---|---|---|---|
| | 5 | 2.5 | 1.25 | 0.625 | 5 | 2.5 | 1.25 | 0.625 |
| Oats | 0 | 0 | 0 | 0 | 0 | 0 | 0 | 0 |
| Wheat | 0 | 0 | 0 | 0 | 0 | 0 | 0 | 0 |
| Barley | 0 | 0 | 0 | 0 | 0 | 0 | 0 | 0 |
| Corn | 0 | 0 | 0 | 0 | 0 | 0 | 0 | 0 |
| Bent grass | 0 | 0 | 0 | 0 | 0 | 0 | 0 | 0 |
| Rye grass | 0 | 0 | 0 | 0 | 0 | 0 | 0 | 0 |
| Foxtail | 0 | 0 | 0 | 0 | 0 | 0 | 0 | 0 |
| Beets | 0 | 0 | 0 | 0 | 24 | 32 | 0 | 0 |
| Lambsquarter | 100 | 75 | 0 | 0 | 100 | 100 | 100 | 100 |
| Chrysanthemum | 66 | 49 | 27 | 0 | 0 | 0 | 0 | 0 |
| Gaillet | 0 | 0 | 0 | 0 | 0 | 0 | 0 | 0 |
| Mustard | 83 | 48 | 0 | 0 | 94 | 57 | 43 | 0 |
| Rumex | 0 | 0 | 0 | 0 | 100 | 100 | 100 | 29 |
| Clover | 0 | 0 | 0 | 0 | 0 | 0 | 0 | 0 |

Various modifications of the compounds and methods of the invention may be made without departing from the spirit or scope thereof and it should be understood that the invention is intended to be limited only as defined in the appended claims.

We claim:

1. A urea of the formula

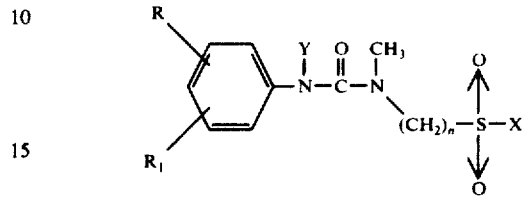

wherein R and $R_1$ are individually selected from the group consisting of hydrogen, chlorine, bromine, trifluoromethyl, lower alkyl of 1 to 6 carbon atoms and lower alkoxy of 1 to 6 carbon atoms, $n$ is 0, X is lower alkyl of 1 to 6 carbon atoms optionally substituted with a halogen, Y is selected from the group consisting of hydrogen and alkyl of 1 to 4 carbon atoms and the dotted lines indicate that the compound may contain no oxygen bound to the sulfur atom or may be in sulfoxide or sulfonyl form.

2. A compound of claim 1 wherein Y is hydrogen and X is lower alkyl of 1 to 6 carbon atoms.

3. A compound of claim 1 wherein Y is hydrogen, X is alkyl of 1 to 6 carbon atoms optionally substituted with halogen, and the sulfur atom is not oxidized.

4. A compound of claim 1 which is N-methyl-N-ethylthio-N'-(3,4-dichlorophenyl)-urea.

5. A compound of claim 1 which is N-methyl-N-ethylthio-N'-(3-trifluoromethylphenyl)-urea.

6. A compound of claim 1 which is N-methyl-N-ethylthio-N'-(3-chloro-4-methylphenyl)-urea.

7. A compound of claim 1 which is N-methyl-N-ethylthio-N'-(3-chloro-4-methoxyphenyl)-urea.

8. A compound of claim 1 which is N-methyl-N-ethylthio-N'-(4-bromophenyl)-urea.

9. A compound of claim 1 which is N-methyl-N-isopropylthio-N'-(3',4'-dichlorophenyl)-urea.

10. A herbicidal composition comprising an effective amount of a compound of claim 1 and an inert carrier.

11. A method of combatting weeds comprising applying to the soil before the emergence of weeds a herbicidally effective amount of a compound of claim 1.

12. A method of combatting weeds comprising contacting weeds with a herbicidally effective amount of a compound of claim 1.

* * * * *